United States Patent [19]

Hadvary et al.

[11] Patent Number: 4,598,089

[45] Date of Patent: Jul. 1, 1986

[54] LEUCINE DERIVATIVES

[75] Inventors: Paul Hadvary, Biel-Benken; Erich Hochuli, Arisdorf; Ernst Kupfer, Basel; Hans Lengsfeld, Reinach; Ernst K. Weibel, Pratteln, all of Switzerland

[73] Assignee: Hoffmann-La Roche Inc., Nutley, N.J.

[21] Appl. No.: 621,827

[22] Filed: Jun. 18, 1984

[30] Foreign Application Priority Data

Jun. 22, 1983 [CH] Switzerland ............... 3415/83

[51] Int. Cl.$^4$ ............... C07D 305/12; C12P 17/02; A61K 31/365
[52] U.S. Cl. ............... 514/449; 549/263; 549/328; 514/909; 435/123; 435/886
[58] Field of Search ............... 549/263, 328; 435/123; 514/449

[56] References Cited

U.S. PATENT DOCUMENTS

| | | | |
|---|---|---|---|
| 4,189,438 | 2/1980 | Umezawa et al. | 549/263 |
| 4,202,824 | 5/1980 | Umezawa et al. | 549/263 |
| 4,242,453 | 12/1980 | Umezawa et al. | 435/123 |
| 4,358,602 | 11/1982 | Umezawa et al. | 435/123 |

OTHER PUBLICATIONS

Derwent 70402 D/39 (Mar. 1980).
Derwent 87970 B/49 (May 1978).

Primary Examiner—Glennon H. Hollrah
Assistant Examiner—Dara Dinner
Attorney, Agent, or Firm—Jon S. Saxe; Bernard S. Leon; George W. Johnston

[57] ABSTRACT

Novel compounds of the formula

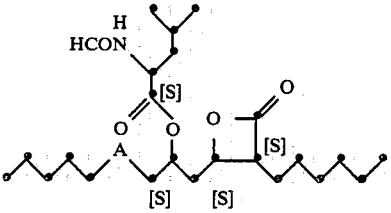

wherein A signifies the group

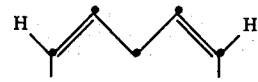

or —$(CH_2)_5$—, which inhibit pancreas lipase and can be used for the control or prevention of obesity and hyperlipaemia, are disclosed. The inventive compounds can be produced by the cultivation of microorganism *Streptomyces toxytricini*, identified as NRRL 15443.

20 Claims, No Drawings

LEUCINE DERIVATIVES

BACKGROUND

The present invention concerns N-formylleucine derivatives which are useful in the treatment of obesity and hyperlipaemia.

SUMMARY OF THE INVENTION

The present invention is concerned with compounds of the formula

[Structure I]

wherein A signifies the group

[Structure]

or —(CH$_2$)$_5$—.

Formula I above embraces (2S,3S,5S,7Z,10Z)-5-[(S)-2-formamido-4-methyl-valeryloxy]-2-hexyl-3-hydroxy-7,10-hexadecadienoic acid lactone of the formula

[Structure Ia]

(i.e., lipstatin,) and (2S,3S,5S)-5-[(S)-2-formamido-4-methyl-valeranyloxy]-2-hexyl-3-hydroxy-hexadecanoic acid lactone of the formula

[Structure Ib]

(i.e., tetrahydrolipstatin).

These compounds are novel and have valuable pharmacological properties. In particular, they inhibit pancreas lipase and can be used in the control or prevention of obesity and hyperlipaemia.

Objects of the present invention are the compounds of formula I above per se and as pharmaceutically active substances, the manufacture of these compounds, medicaments and industrially-produced foodstuffs containing a compound of formula I, their production as well as the use of these compounds in the control or prevention of illnesses. More particularly, the invention concerns methods for preventing or treating obesity or hyperlipaemia in an afflicted mammal.

DETAILED DESCRIPTION OF THE INVENTION

The present invention is concerned with compounds of the formula

[Structure I]

wherein A signifies the group

[Structure]

or —(CH$_2$)$_5$—.

Formula I above embraces (2S,3S,5S,7Z,10Z)-5-[(S)-2-formamido-4-methyl-valeryloxy]-2-hexyl-3-hydroxy-7,10-hexadecadienoic acid lactone of the formula

[Structure Ia]

which is referred to hereinafter as lipstatin, and (2S,3S,5S)-5-[(S)-2-formamido-4-methyl-valeryloxy]-2-hexyl-3-hydroxy-hexadecanoic acid lactone of the formula

[Structure Ib]

which is referred to hereinafter as tetrahydrolipstatin.

These compounds are novel and have valuable pharmacological proprties. In particular, they inhibit pancreas lipase and can be used in the control or prevention of obesity and hyperlipaemia.

The present invention is also concerned with pharmaceutical compositions for preventing and treating obesity or hyperlipaemia comprising a compound of formula I and a pharmaceutically acceptable carrier material.

The invention also concerns methods for preventing or treating obesity or hyperlipaemia in an afflicted mammal wherein compound I is administered to the mammal in an amount which is effective in preventing or treating obesity or hyperlipaemia.

The invention also is directed to a commercially-produced foodstuff comprising compound I admixed with a material suitable for consumption.

As used herein, [S] indicates the absolute configuration of compound I in the S-form. More particularly, the applicable carbon atoms in formula I having the S-configuration are noted with enlarged circles in the following formula:

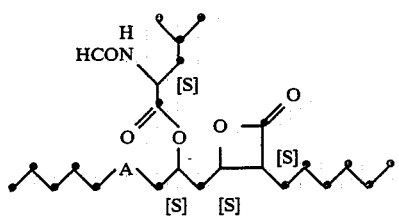

wherein A is as above.

The digestion of fats (triglycerides) taken in with the food is effected in the intestine by pancreas lipase. The pancreas lipase cleaves the primary ester bonds of triglycerides, whereby free fatty acids and 2-monoglycerides result as products. These products can then be resorbed and utilized. By inhibiting the pancreas lipase the aforementioned cleavage of the foot fats and therewith also the resorption and utilization of these substances is partially prevented; the triglycerides are excreted in unchanged form.

The inhibition of pancreas lipase by the compounds of formula I can be demonstrated experimentally by registering tritrimetrically the oleic acid liberated in the cleavage of triolein by pig pancrease lipase. An emulsion which contains 1 mM taurodeoxycholate, 9 mM taurodeoleate, 0.1 mM cholesterol, 1 mM egg lecithin, 15 mg/ml BSA (i.e., bovine serum albumine), 2 mM Tris-HCl, 100 mM sodium chloride, 1 mM calcium chloride and the substrate triolein is treated with the compound of formula I dissolved in ethanol or dimethyl sulphoxide (10% of the emulsion volume) and the reaction is started by the addition of 100 µl (175 U) of pig pancreas lipase. the pH is held at 8 during the reaction by the addition of sodium hydroxide. The $IC_{50}$ is calculated from the consumption of sodium hydroxide determined during 10 minutes. The $IC_{50}$ is that concentration at which the lipase reactivity is inhibited to half of the maximum. Table I hereinafter contains $IC_{50}$ values determined for the compounds of formula I and data concerning the acute toxicity ($LD_{50}$ after single oral administration to mice).

TABLE I

| Test compound | $IC_{50}$ in µg/ml | $LD_{50}$ in mg/kg p.o. |
|---|---|---|
| Lipstatin | 0.07 | >4000 |
| Tetrahydrolipstatin | 0.18 | — |

The inhibition of the resorption of fats taken in with the food, which is brought about by the inhibition of pancreas lipase, can be demonstrated in a double-labelling experiment on mice. For this purpose, there is administered to the test animals a test meal, which contains $^3$H-triolein and $^{14}$C-oleic acid, and a compound of formula I. By measuring the radioactivity there is then determined the amount of $^3$H-triolein and $^{14}$C-oleic acid (in % of the amount administered) excreted with the feces. The results set forth in Table II hereinafter show that in comparison to untreated control animals the excretion of unaltered triglyceride increases greatly and the excretion of oleic acid remains largely unchanged.

TABLE II

| Test compound | Number of experimental animals | Dosage | Excretion in % of the amount administered | |
|---|---|---|---|---|
| | | | Triolein | Oleic acid |
| Controls | 12 | — | 3.5 ± 0.3 | 10.1 ± 0.6 |
| Lipstatin | 6 | 40 mg/kg* | 56.8 ± 13 | 13.8 ± 5.6 |

*The experiments were carried out with a preparation which contained about 10% lipstatin. The dosage specified is the amount of lipstatin administered.

The compounds of formula I can be manufactured in accordance with the invention by the following procedure:

(a) for the manufacture of the compound of formula Ia, aerobically cultivating a microorganism of the species Streptomyces toxytricini which produces this compound in an aqueous culture medium which contains suitable carbon and nitrogen sources and inorganic salts and separating the compound of formula Ia produced from the culture broth, or (b) for the manufacture of the compound of formula Ib, hydrogenating the compound of formula Ia.

Streptomycetes strains which produce lipstatin, the compound of formula Ia, can be isolated from soil samples from various locations. An example is the microorganism isolated from a soil sample found in Mallorca, Spain, which was given the laboratory designation Streptomyces sp. 85-13 and which has been identified by CBS, Baarn (Netherlands) as *Streptomyces toxytricini* Preobrazhenskaya & Sveshnikova (see Bergey's Manual of Determinative Bacteriology, 8th Edition, page 811). It thereupon received the new designation Streptomyces toxytricini 85-13. A lyophilized sample of this strain was deposited on the 14th June 1983 at the Agricultural Research Culture Collection, Peoria, Ill., under the designation NRRL 15443.

A description of the identification of Streptomyces sp. 85-13 is given hereinafter:

Media

The composition of the media used is described in Int. J. Syst. Bacteriol 1966, 16, 3; 313–321.

Nonomura diagram

Nonomura used the results of the International Streptomyces Project (ISP) for the classification of the Streptomycetes speces (J. Ferment. Technol. 1974, 52, 2).

Colours

The names and code numbers of the aerial mycelium come from Tresner & Backus "System of color wheels for streptomycete taxonomy". The colours of the reverse of the colonies come from H. Prauser's selection from Baumann's "Farbtonkarte Atlas I".

Methodology

This was carried out according to the ISP methods (see Int. J. Syst. Bacteriol, 1966, 16, 3; 313–340).

I. Agar cultures after 16 days at 28° C. (double determination)

(a) Oatmeal agar

Growth: abundant; colonies: thin, spreading; aerial mycelium: velutinous, pinkish brown (Light Brown 57); reverse of the colonies: yellowish (Pr. Coo-3-m) with broad purple-grey (Pr. Oc-6-x) margin; soluble pigments: doubtful.

(b) Starch-salt agar

Growth: good; colonies: thin, spreading; aerial mycelium: velutinous, pinkish brown (Light Brown 57) with white sectors; reverse of the colonies: dark straw coloured [Pr. Coo (Cr) 5a], margin and some other areas pinkish (Pr. Oc-5-b) with some dark reddish brown [Pr. O-5-S(r)] spots; soluble pigments: doubtful. The diastatic action is excellent.

(c) Glycerine-asparagine agar

Growth: good; colonies: thin, spreading; aerial mycelium: velutinous, pale pinkish brown (R4ec: Grayish Yellowish Pink); reverse of the colonies: orange (Pr. Oc-3-m/r); soluble pigments: pale pinkish brown.

(d) Yeast malt agar

Growth: good; colonies: thin, spreading; aerial mycelium: reddish brown (4ge: Light Grayish Reddish Brown 45); reverse of the colonies: yellow (Pr. Coo-4-5) and dark brown (Pr. Oc-5-r); soluble pigments: very pale yellowish brown.

II. Agar cultures after 62 days at 28° C. (double determination)

(a) Oatmeal agar

Growth: good; colonies: thin, spreading; aerial mycelium: powdery velutinous, cinnamon coloured [R-4ie: Light Brown (57)-Cork Tan] with broad, paler margin [R. 5gc: Light Reddish Brown (4.2)-Peach Tan]; reverse of the colonies: yellowish-brown with ochre-yellow (Pr. Coo-3-a) margin, slightly greyish towards the bright (Pr.Oc-4-r) centre; soluble pigments: pale ochre-brown.

(b) Starch-salt agar

As an oatmeal agar, but with a move greyish brown reverse (Pr. Oc-6-c) and with dark brown (Pr. Oc-4-r) spots and rings at the ends of the cross-hatches.

(c) Glycerine-asparagine agar

As on starch-salt agar, but paler light beige (5ec: Grayish yellowish Pink 32-Dusty Peach); Reverse: ochre-yellow [Pr. Coo (=Cr)-4-b], paler in the centre; no soluble pigments.

(d) Yeast-malt agar

Growth: fair; colonies: almost as on satmeal agar, but with very thin, pale grey margin; reverse: dark yellow (Pr. Coo-4-b), dark brown in submerginal areas; soluble pigments: doubtful.

III. Melanoid pigments

Peptone-yeast extract agar: negative after 24 hours, positive after 48 hours; tyrosine agar: positive after 24 hours, positive after 48 hours.

IV. Morphology of the sporulating aerial mycelium
  Section: spira-retinaculum apertum. Sympodial branched type. Spirals often irregular, with up to 5 coils often of different diameters.

V. Utilization of carbon sources No growth or only sparing growth on arabinose, xylose, inositol, mannitol, fructose, rhamnose, saccharose, raffinose.

VI. Spores

Oval to cylindrical-oval, sometimes of irregular size, smooth-walled. Spore chains with more than 10 spores.

VII. Nonomura diagram

R(Gy) 100 SRA sm($\pm$) ($\pm$) ($\pm$)————

All Streptomycetes strains which produce the lipase inhibitor lipstatin are suitable for the purpose of the present invention, especially Streptomyces toxytricini 85–13, NRRL 15443, and its subcultures, mutants and variants.

The cultivation of these microorganisms for the manufacture of lipstatin can be carried out according to various fermentation methods. It can be carried out, for example, in shaking flasks or in 10 l or 200 l and 1000 l fermentors. A fixed amount of spore material or mycelium or a lipstatin-producing strain is introduced into a liquid medium which contains suitable carbon and nitrogen sources and salts required for the growth and the mixture is aerobically incubated at a temperature of 20°–37° C. for 1–6 days. Suitable carbon sources are, for example, dextrin, glucose, starch, ribose and glycerine. Suitable nitrogen sources are, for example, yeast extract, peptone or soya meal. Preferred salts are ammonium, magnesium and calcium salts. The fermentation is carried out at pH 6–8.

The isolation of the lipstatin is carried out according to methods which are known per se and which are familiar to any person skilled in the art. For example, it can be carried out as follows:

After completion of the fermentation the fermentation broth is centrifuged, whereupon 60–90% of the activity is found in the cell mass and the remainder is found in the centrifugate. The cell mass can then be treated with a lowr alcohol such as methanol and ethanol and extracted with the same solvent. The centrifugate can be extracted with a suitable organic solvent (e.g. with methylene chloride or ethyl acetate). The material produced from the extracts contains the desired lipstatin and can be enriched and purified by chromatographic methods. Suitable methods are, for example, multiplicative extraction with the system hexane/methanol/water (50:40:9), filtration chromatography over silica gel while eluting with chloroform, column chromatography on silica gel while eluting with hexane, ethyl acetate and mixtures thereof, chromatography on apolar carrier materials while eluting with polar solvents such as methanol (reversed-phase chromatography) and high pressure liquid chromatography.

The Examples hereinaftr contain detail information relating to the cultivation of Streptomyces toxytricini 85–13 and the isolation of the lipstatin.

Tetrahydrolipstatin, the compound of formula Ib, can be manufactured by hydrogenating lipstatin in the presence of a suitable catalyst. Examples of catalysts which can be used are palladium/carbon, platinum oxide, palladium and the like. Suitable solvents are, for example, lower alcohols such as methanol and ethanol. The hydrogenation is preferably carried out at low hydrogen pressures and at room temperature (about 23° C.)

The compounds of formula I can be used as medicaments, for example in the form of pharmaceutical preparations. Illustratively, the pharmaceutical preparations can be administered orally, for example in the form of tablets, coated tablets, dragées, hard and soft gelatine capsules, solutions, emulsions or suspensions. If desired, the compounds also can be administered parenterally.

For the manufacture of pharmaceutical preparations the compounds of formula I can be processed with pharmaceutically inert, inorganic or organic carriers. Examples of carriers which can be used for tablets, coated tablets, dragées and hard gelatine capsules are lactose, maize starch or derivatives thereof, talc, stearic acid or its salts and the like. Suitable carriers for soft gelatine capsules are, for example, vegetable oils, waxes, fats, semi-solid and liquid polyols and the like; depending on the nature of the active ingredient no carriers are, however, generally required in the case of soft gelatine capsules. Suitable carriers for the manufacture of solutions and syrups are, for example, water polyols, saccharose, invert sugar, glucose and the like.

Moreover, the pharmaceutical preparations can contain preserving agents, solubilizers, stabilizing agents, wetting agents, emulsifying agents, sweetening agents, colouring agents, flavouring agents, salts for varying the osmotic pressure, buffers, coating agents or antioxidants. They can also contain still other therapeutically valuable substances.

As mentioned earlier, medicaments containing a compound of formula I are also an object of the present invention as is a process for the manufacture of these medicaments, which process comprises bringing a compound of formula I and, if desired, one or more other therapeutically valuable substances into a galenical administration form. As mentioned earlier, the compounds of formula I can be used in the control or prevention of illnesses and especially in the control or prevention of obesity and hyperlipaemia. The dosage can vary within wide limits and is, of course, fitted to the individual requirements in each particular case. In general, in the case of oral administration a daily dosage of about 0.1 mg to 100 mg/kg body weight of compound I is appropriate.

Preferably, the pharmaceutical compositions of formula I in unit dosage form contain about 5% to 95% by weight of compound I to the total composition. A range of 10% to 50% is preferred.

The compounds of formula I can also be added to industrially-produced foodstuffs, especially to fats, oils, butter, margarine, chocolate and other confectionery goods. Such industrially-produced foodstuffs and their production are also objects of the present invention.

The following Examples illustrate the present invention in more detail, but are not intended to limit its extent. All temperatures are given in degrees Celsius (°C.). Room temperature is about 23° C. Unless otherwise indicated, precentages and ratios relating to solvents and expressed in volume, and the remaining percentages are expressed in weight. Unless indicated otherwise, all Examples were carried out as written. A Lobar column Lichoprep RP-8, size C, is a lowpressure reverse phase column, commercially available from Merck Co.

EXAMPLE 1

(a) Fermentation:

A shaking flask containing pre-culture medium 391 is inoculated with spores of Streptomyces toxytricini 85–13 (or vegetative mycelium thereof) and aerobically incubated as a shaking culture at 28° C. for 72 hours. About 2–5 vol.% of this culture is used to inoculate a fermentor preculture of 10 l containing pre-culture medium 391. Incubation is carried out at 28° for 3 days with aeration of 1 vvm and stirring at 400 rpm. This 10 l pre-culture is used to inoculate a 200 l production fermentor containing production medium N7. Fermentation is carried out at 28° for 124 hours with aeration of 1.0 vvm and stirring at 150 rpm. Regular analyses show after 124 hours an extracellular lipase-inhibiting activity of 53 $IC_{50}$/ml.

The pre-culture medium 391 (pH 7.0) has the following composition: 3% maize starch, 4% dextrin, 3% soya meal, 0.2% $(NH_4)_2SO_4$, 0.6% $CaCO_3$ and 0.8% soya oil. The pH was adjusted to 7. The production medium N 7 (pH 7.0) has the following composition: 1% potato starch, 0.5% glucose, 1% ribose, 0.5% glycerine, 0.2% peptone, 2% soya meal and 0.2% $(NH_4)_2SO_4$.

(b) Working-up:

The fermentation broth is centrifuged by means of a tube centrifuge, whereby there are obtained 175 l of culture filtrate and 12 kg of mycelium. The mycelium is discarded. The culture filtrate is heated to 80° for 10 minutes, cooled, again centrifuged and concentrafed to 50 l at 30° in vacuo. This concentrate is extracted with 50 l of hexane using a continuously operating extractor, the emulsion obtained is mixed with 50 l of hexane/ethyl acetate (1:1) and the organic phase is separated. This is dried ovr sodium sulphate and evaporated, there being obtained 199 g of crude extract I. The aqueous phase is diluted with water to 100 l and extracted with 100 l of ethyl acetate. After evaporation of the ethyl acetate solution, there are obtained 49 g of crude extract II. The aqueous phase is subsequently extracted once more with 100 l of ethyl acetate, whereby 78 g of crude extract III are obtained after evaporation.

(c) Purification:

The crude extracts II and III are filtered in three portions over in each case 1 kg of silica gel 60 (0.040–0.063 mm particle size), whereby the elution is carried out with chloroform (column: 10×100 cm). 18.3 g of enriched material are obtained in this manner. 178 g of this substance are again filtered over 1 kg of silica gel while eluting with chloroform. 5.29 g of active material are thus obtained. 802 mg of this substance are purified by reversed-phase chromatography on a commercially obtainable Lobar column (Lichoprep RP-8, size C) while eluting with methanol. There are obtained 158 mg of (2S,3S,5S,7Z,10Z)-5-[(S)-2-formamido-4-methyl-valeryloxy]-2-hexyl-3-hydroxy-7,10-hexadecadienoic acid lactone (lipstatin) which is a yellowish oil at room temperature. It is waxy-crystalline at low temperatures.

Microanalysis (dried for 20 hours in a high vacuum at 50°):

Calculated for $C_{29}H_{49}N_1O_5$ (491.713): C 70.84, H 10.04, N 2.85. Found C 70.85, H 9.97, N 2.59.

Optical rotation: $[a]_D^{20} = -19.0°$ (c=1 in chloroform).

Mass spectrum (chemical ionization with $NH_3$ as the reagent gas): Peaks at, inter alia, m/z 509 ($M+NH_4^+$) and 492 ($M+H^+$).

IR spectrum (film): Bands at, inter alia, 3318, 3012, 2928, 2558, 2745, 1823, 1740, 1673, 1521, 1382, 1370, 1250, 1191 cm$^{-1}$.

The absolute configuration could be established by chemically degrading the lipstatin and comparing the fractions obtained with known substances.

EXAMPLE 2

(a) Fermentation

A 200 l fermentor containing production medium N 16 is inoculated with a pre-culture of Streptomyces toxytricini 85-13 (shaking flasks and then 10 l fermentation) prepared in accordance with Example 1. The production medium N 16 corresponds to production medium N 7 used in Example 1, but also contains 0.1% pig lard. The fermentation is carried out as described in Example 1 for 120 hours. After 120 hours, the intracellular lipase-inhibiting activity amounts to 71 $IC_{50}$/ml of fermentation broth and the extracellular lipase-inhibiting activity amounts to 4 $IC_{50}$/ml of fermentation broth.

(b) Working-up

After completion of the fermentation, the fermentation broth is heated to 80° for 10 minutes, subsequently cooled and the cell mass is separated using a tube centrifuge. By two-fold centrifugation there are obtained 11.4 kg of mycelium; the culture filtrate is discarded. The mycelium is triturated in 70 l of methanol for 30 minutes, whereupon the suspension obtained is suction filtered. The filter cake is again triturated with 50 l of methanol and suction filtered. The combined methanolic extracts are concentrated to 1.8 l. This concentrate is extracted three times with 2 l of butyl acetate each time. 160 g of crude extract are obtained from the combined organic phases after evaporation.

(c) Purification

This crude extract is purified by multiplicative extraction with the system hexane/methanol/water (5:4:0:9). The active substance is firstly transferred from the lower phase (lp) into the upper phase (up). 160 g of crude extract are dissolved in 4 l of lp and stirred in a stirring vessel with 4 l of up. After separating the up, the lp is extracted a second time with 4 l of fresh up. A stable emulsion forms and to this there are added 4 l of lp and 4 l of up, whereupon a good phase separation is achieved. After separating the up, the lp is extracted twice more with 8 l of fresh up. The combined up give 90.3 g of extract after evaporation. The extraction lp is discarded. The active substance is now transferred from the up into the lp. 90.3 g of the above extract are dissolved in 4 l of up and extracted with 4 l of lp. After phase separation, the up is extracted a further three times with fresh lp. The up is subsequently discarded. The combined lp are concebtrated to 0.7 l of aqueous phase and this is extracted eight times with a total of 0.2 l of ethyl acetate. 25.8 g of product are obtained after evaporation. The extracted aqueous phase is discarded. The further purification of this material is carried out by filtration over 1 kg of silica gel 60 (0.040–0.063 mm particle size; column 10×100 cm) while eluting with chloroform. There are obtained 649 mg of product which is chromatographed on a Lobar column (Lichoprep RP-8, size C) while eluting with methanol (reversed-phase chromatography). There are obtained 204 mg of lipstatin which is pure according to thin-layer chromatography.

EXAMPLE 3

138 mg of lipstatin are dissolved in 10 ml of ethanol and the solution is treated with 60 mg of 5 percent palladium/carbon and stirred at room temperature for 3 hours in a hydrogen atmosphere (balloon). The catalyst is subsequently centrifuged off. The hydrogenation product is chromatographed over a short silica gel column (1×5 cm) with chloroform. There are obtained 112 mg of (2S,3S,5S)-5-[(S)-2-formamido-4-methylvaleryloxy]-2-hexyl-3-hydroxyhexadecanoic acid lactone (tetrahydrolipstatin) as a waxy, slightly yellow solid.

Optical rotation: $[\alpha]_D^{20} = -32.0°$ (c=1 in chloroform).

Mass spectrum (chemical ionization with $NH_3$ is the reagent gas): Peaks at, inter alia, m/z 513 ($M+NH_4^+$); 496 ($M+H^+$) and 452 ($M+H^+-CO_2$).

IR spectrum (film): Bands at, inter alia, 3332, 2956, 2921, 2853, 1838, 1731, 1709, 1680, 1665, 1524, 1383, 1249 and 1200 cm$^{-1}$.

$^1$H-NMR spectrum (270 MHz, $CDCl_3$): 0.89 (6H); 0.97 (6H); 1.15–1.5 (27H); 1.5–1.85 (6H); 1.9–2.25 (2H); 3.24 (1H); 4.32 (1H); 4.68 (1H); 5.03 (1H); 6.43 (1H); 8.07 and 8.21 (1H) ppm.

EXAMPLE 4

(a) Fermentation

A 2 l shaking culture flask containing pre-culture medium 391 is inoculated with spores of an agar slant culture of Streptomyces toxytricini 85-13 and aerobically incubated at 28° C. for 72 hours. Thereafter, the 2 l preculture is transferred into a 50 l fermentor containing production medium N 16 and incubated at 28° C. for 77 hours with 0.5 vvm aeration. This 50 l pre-culture is used to inoculate a 1000 l fermentor containing medium N 16. This production fermentation is carried out at 28° C. and 0.5 vvm aeration for 91 hours, whereby a lipstatin titre of 73 $IC_{50}$/ml intracellularly and 16 $IC_{50}$/ml extracellularly is achieved. The entire fermentation broth is cooled to 2° C. and centrifuged, whereby there are obtained 41 kg of moist biomass which are frozen at −20° C.

(b) Working-up 37 kg of mycelium are melted at 4° C. and homogenized with about 40 l of water in a mixer. The thinly liquid suspension obtained is treated with 140 l of methanol and stirred for 20 minutes. The mixture is subsequently suction filtered over a cloth filter, whereupon the filter cake is extracted further with 140 l of methanol. The methanol extracts are concentrated at 30° C. to about 22 l. The concentrate obtained is diluted with ater to 50 l and extracted three times in a stirring vessel with 50 l of hexane/ethyl acetate (1:1) each time. In the second and third extractions there are obtained emulsions which can be broken by the addition of about 1.4 kg and 0.5 kg of sodium chloride, respectively. The combined organic extracts are concentrated, dried over sodium sulphate and evaporated to an oily residue. 428 g of crude extract are obtained.

(c) Purification

This crude extract is filtered in four portions over in each case 1 kg of silica gel 60 (0.040–0.063 mm particle size), whereby the elution is carried out with chloroform (column: 10×100 cm). There are obtained 70 g of enriched preparation which is filtered in two portions over in each case 1 kg of silica gel 60 while eluting with hexane/ethyl acetate (gradient from 9:1 to 4:1). There are obtained 4.2 g of active material which is purified in four portions by reversed-phase chromatography on a Lobar column (Lichoprep RP-8, size C) while eluting with methanol. 1.77 g of lipstatin are obtained.

EXAMPLE A

Manufacture of soft gelatine capsules of the following composition:

|  | Amount per capsule |
|---|---|
| Lipstatin | 50 mg |
| NEOBEE M-5 | 450 µl |

The solution of the active substance in NEOBEE M-5 is filled into soft gelatine capsules of suitable size. NEOBEE M-5 is a mixture of triglycerides commonly used for pharmaceutical preparations.

We claim:

1. A compound of the formula

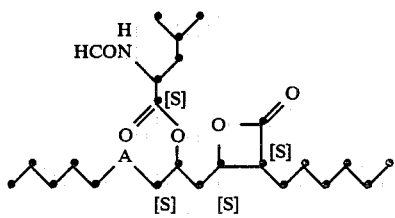

wherein A is the group

or —(CH$_2$)$_5$—.

2. The compound of claim 1, (2S,3S,5S,7Z,10Z)-5-[(S)-2-formamido-4-methyl-valeryloxy]-2-hexyl-3-hydroxy-7,10-hexadecadienoic 1,3 acid lactone.

3. The compound of claim 1, (2S,3S,5S)-5-[(S)-2-formamido-4-methyl-valeryloxy]-2-hexyl-3-hydroxy-hexadecanoic 1,3 acid lactone.

4. A pharmaceutical composition for administration to a patient comprising
(a) about 5% to about 95% of a compound of formula

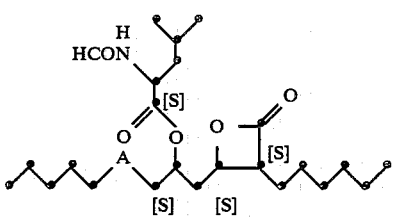

wherein A is the group

or —(CH$_2$)$_5$— said composition being present in a amount sufficient to supply about 0.1 to about 100 mg of compound I per kilogram of body weight of the patient per day; and (b) 5% to 95% of a pharmaceutically acceptable inert carrier material, said composition being formulated in a unit dosage form.

5. The composition of claim 4 wherein said composition is formulated in an oral unit dosage form.

6. The composition of claim 5 wherein said oral unit dosage form is a tablet, dragee, capsule, solution, emulsion or suspension.

7. The composition of claim 4 wherein compound I is (2S,3S,5S,7Z,10Z)-5-[(S)-2-formamido-4-methyl-valeryloxy]-2-hexyl-3-hydroxy-7,10-hexadecadienoic 1,3 acid lactone.

8. The composition of claim 4 wherein compound I is (2S,3S,5S)-5-[(S)-2-formamido-4-methyl-valeryloxy]-2-hexyl-3-hydroxy-hexadecanoic 1,3 acid lactone.

9. A method of treating obesity in an afflicted mammal comprising administering to the mammal a compound of the formula

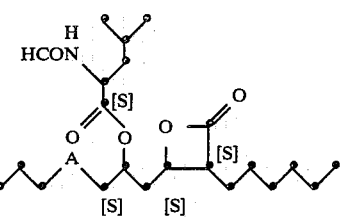

wherein A is the group

or —(CH$_2$)$_5$— in an amount which is effective in treating obesity.

10. The method of claim 9 wherein compound I is (2S,3S,5S,7Z,10Z)-5-[(S)-2-formamido-4-methyl-valeryloxy]-2-hexyl-3-hydroxy-7,10-hexadecadienoic 1,3 acid lactone.

11. The method of claim 9 wherein compound I is (2S,3S,5S)-5-[(S)-2-formamido-4-methyl-valeryloxy]-2-hexyl-3-hydroxy-hexadecanoic 1,3 acid lactone.

12. The method of claim 9 wherein compound I is administered in a daily dose of about 0.1 mg to 100 mg/kg body weight of the mammal.

13. A method of treating hyperlipaemia in an afflicted mammal comprising adminstering to the mammal a compound of the formula

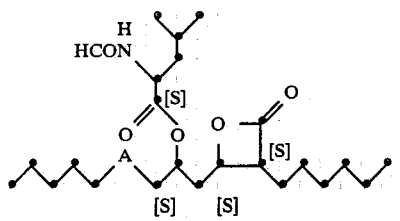

wherein A is the group

or —(CH₂)₅—, in an amount which is effective in treating hyperlipaemia.

14. The method of claim 13 wherein compound I is (2S,3S,5S,7Z,10Z)-5-[(S)-2-formamido-4-methyl-valeryloxy]-2-hexyl-3-hydroxy-7,10-hexadecadienoic 1,3 acid lactone.

15. The method of claim 13 wherein compound I is (2S,3S,5S)-5-[(S)-2-formamido-4-methyl-valeryloxy]-2-hexyl-3-hydroxy-hexadecanoic 1,3 acid lactone.

16. The method of claim 13 wherein compound I is administered in a daily dose of about 0.1 mg to 100 mg/kg body weight of the mammal.

17. A method of preventing obesity in a mammal comprising administering to the mammal a compound of the formula

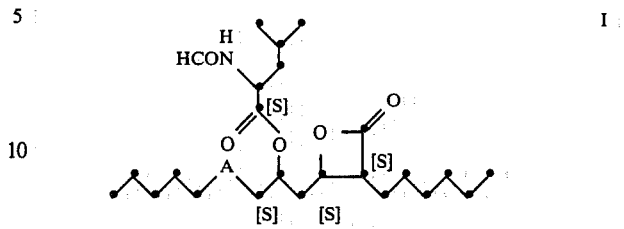

wherein A is the group

or —(CH₂)₅—, in an amount which is effective in preventing obesity by inhibiting pancrease lipase.

18. The method of claim 17 wherein compound I is (2S,3S,5S,7Z,10Z)-5-[(S)-2-Formamido-4-methyl-valeryloxy]-2-hexyl-3-hydroxy-7,10-hexadecadienoic 1,3 acid lactone.

19. The method of claim 17 wherein compound I is (2S,3S,5S)-5-[(S)-2-formamido-4-methyl-valeryloxy]-2-hexyl-3-hydroxy-hexadecanoic 1,3 acid lactone.

20. The method of claim 17 wherein compound I is administered in a daily dose of about 0.1 mg to 100 mg/kg body weight of the mammal.

* * * * *